(12) United States Patent
Kohara et al.

(10) Patent No.: US 8,293,191 B2
(45) Date of Patent: Oct. 23, 2012

(54) METHOD FOR TRANSFERRING DROPLET

(75) Inventors: Yoshinobu Kohara, Yokohama (JP);
Masataka Shirai, Higashimurayama
(JP); Hideyuki Noda, Kokubunji (JP);
Tomoyuki Sakai, Kokubunji (JP);
Kenko Uchida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1404 days.

(21) Appl. No.: 11/675,749

(22) Filed: Feb. 16, 2007

(65) Prior Publication Data

US 2007/0207064 A1 Sep. 6, 2007

(30) Foreign Application Priority Data

Feb. 17, 2006 (JP) .................. 2006-040126

(51) Int. Cl.
*B01L 3/00* (2006.01)
*G01N 21/03* (2006.01)

(52) U.S. Cl. .............. 422/501; 422/82.05; 422/509; 422/519; 422/547; 422/553; 356/246; 73/864; 73/864.31

(58) Field of Classification Search ............... 422/68.1, 422/501–526, 82.01–82.11; 356/246; 73/863.11, 73/864, 864.31
See application file for complete search history.

(56) References Cited

U.S. PATENT DOCUMENTS

| | | | | |
|---|---|---|---|---|
| 3,077,780 A * | 2/1963 | Takatsy | ................. | 73/864.72 |
| 3,191,813 A * | 6/1965 | Duff | .................... | 73/864.72 |
| 7,159,398 B1 * | 1/2007 | Bushnell et al. | ........... | 60/529 |
| 2005/0237605 A1 * | 10/2005 | Vodyanoy et al. | ......... | 359/385 |

FOREIGN PATENT DOCUMENTS

| | | |
|---|---|---|
| JP | 11-271185 | 10/1999 |
| JP | 2002-509274 | 3/2002 |
| JP | 2003-248004 | 9/2003 |
| WO | WO 99/36760 | 7/1999 |

OTHER PUBLICATIONS

Macinnis P. Discovering Bubbles. Internet Archive <http://web.archive.org/web/20051126205812/http://members.ozemail.com.au/~macinnis/scifun/bubbles.htm> (Nov. 26, 2005).*
Lin R. Shape Memory Alloys and Their Applications. Internet Archive <http://web.archive.org/web/20010527040340/http://www.stanford.edu/~richlin1/sma/sma.html> (May 27, 2001).*

* cited by examiner

*Primary Examiner* — Jan Ludlow
(74) *Attorney, Agent, or Firm* — Antonelli, Terry, Stout & Kraus, LLP.

(57) ABSTRACT

The invention provides a method in which an annular or spiral droplet holder formed of wire is used to hold a droplet in a state of being hung therefrom or being contained therein. A means for moving the droplet holder is added to the droplet holder to enable droplet transfer. To merge two droplets, they are brought into contact. To drip the droplet held by a droplet holder formed of wire, the droplet holder is deformed using an external force. A light path which passes through a droplet is set to enable optical measurement. The present invention enables inexpensive, simple droplet transfer. An inexpensive, simple configuration for handling droplets in the fields of chemical analysis, biochemical analysis, and automatic blood analysis can be realized according to the present invention.

12 Claims, 13 Drawing Sheets

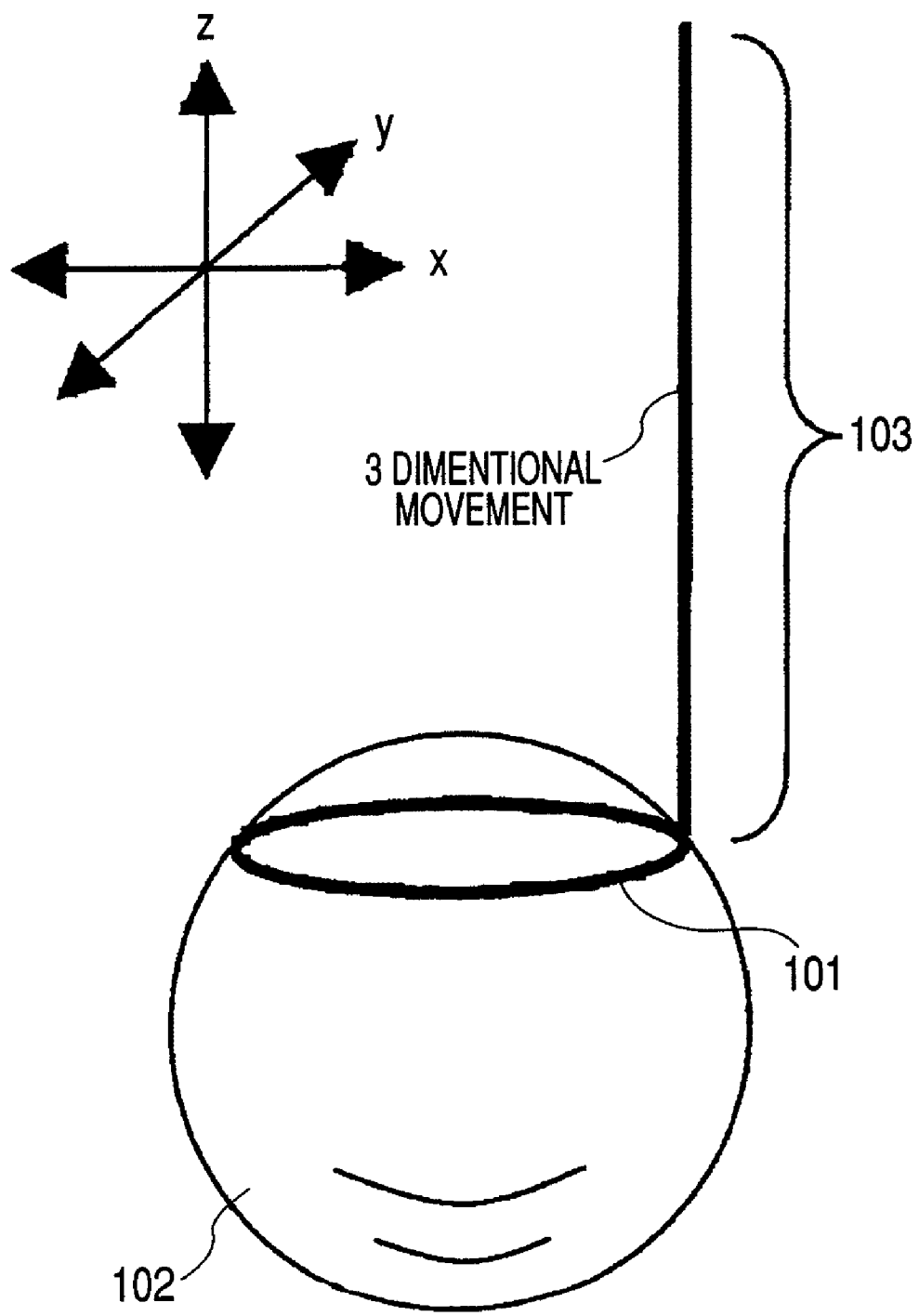

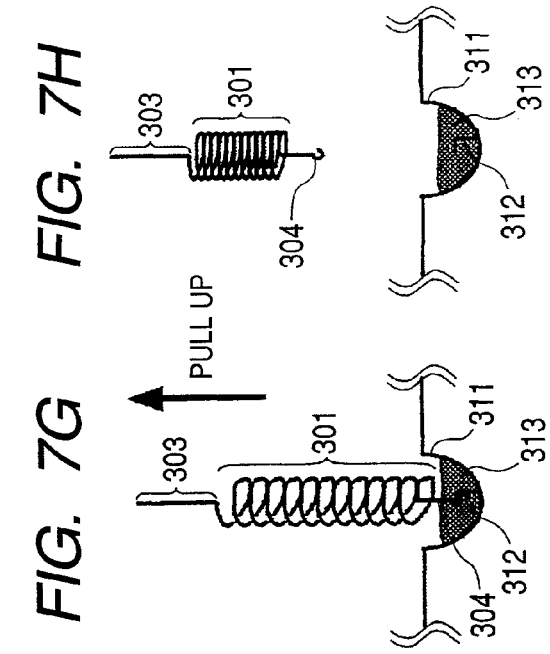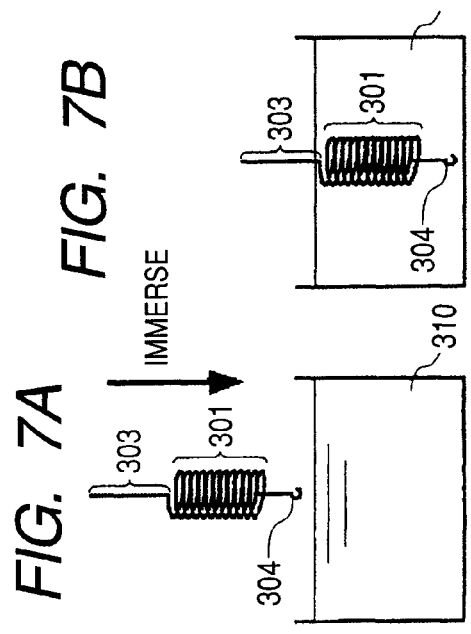

FIG. 8A
FIG. 8B
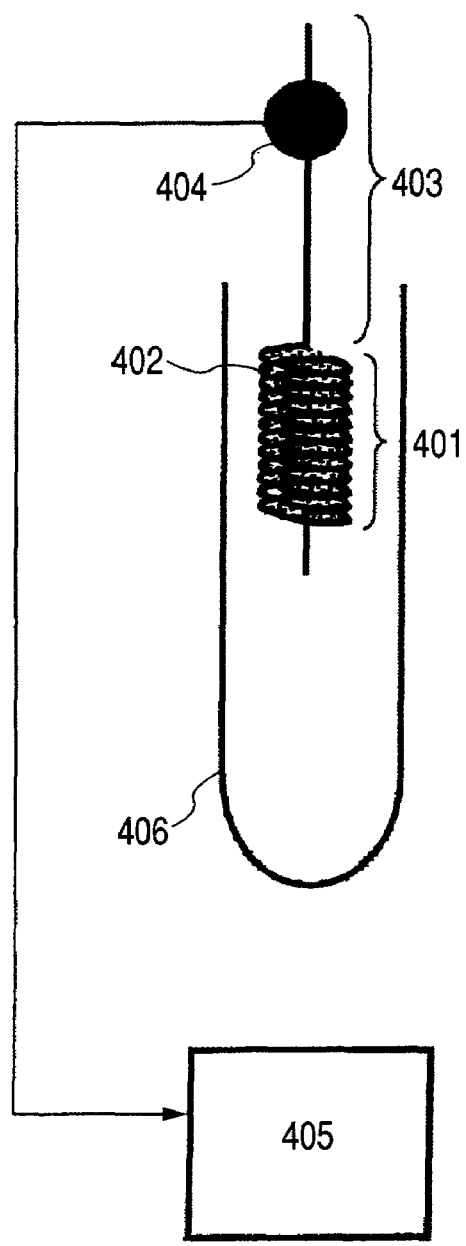
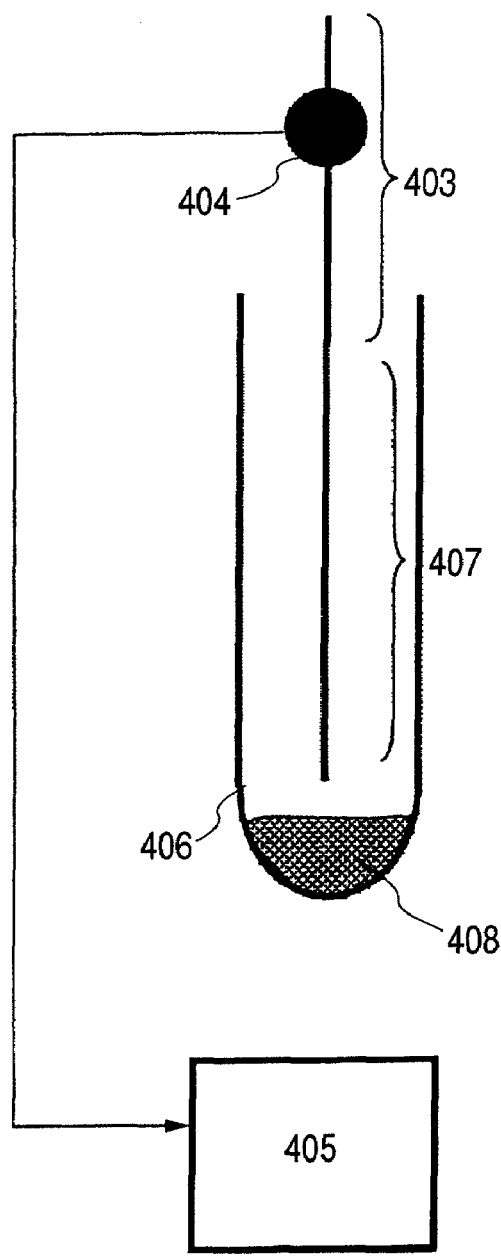

CIRCULATION OR ROTATION

METHOD FOR TRANSFERRING DROPLET

CLAIM OF PRIORITY

The present application claims priority from Japanese application JP 2006-040126 filed on Feb. 17, 2006, the content of which is hereby incorporated by reference into this application.

FIELD OF THE INVENTION

The present invention relates to a method for transferring a droplet of a small volume. The present invention belongs to the fields of small volume droplet formation and dispensing, chemical reactions generated using small volume droplets, and matter generation using small volume droplets. The present invention also belongs to the fields of chemical analysis, biochemical analysis, automatic blood analysis, and immunodiagnosis.

BACKGROUND OF THE INVENTION

Conventional techniques relating to small volume droplet transfer, to which the present invention relates, will be described below. In this specification, "a small volume droplet" refers not to a shape of a liquid droplet, but to a sate of a liquid droplet clearly separated from other liquids.

There are various techniques for transferring small volume droplets. They include, for example, capillary systems and microfluidic MEMS (mechanical and electrical microsystems) In such systems, a surrounded micro-flow path is used, and a droplet to be transferred is placed between gases allowing, for example, a pressure difference between the gases to be used as the power to transfer the droplet. There are also similar systems in which a droplet to be transferred is placed between liquids, instead of gases, which do not mix with the droplet, and the droplet is transferred as in the systems using gases.

Techniques used to transfer a small volume droplet on a plane include EWOD (Electrowetting on Dielectric) and dielectrophoresis techniques. In these techniques, a droplet is placed on a plane or between two planes, and voltage is applied to electrodes installed on or inside the plane or one of the two planes thereby remotely applying a force to move the droplet.

In a technique used to transfer a droplet in air, a droplet is formed and made to fly using a piezoelectric device. A flow site meter used for cell fractionation is an example of a device using the technique. In such a flow site meter, an electric charge is applied to a small volume droplet formed by using a piezoelectric device, the magnitude of the electric charge being dependent on a cell enclosed in the droplet, and the flight curve of the droplet is distorted using a resultant magnetic field so that a required volume of fraction can be sampled. There is also an example application in which droplets are made to fly in two crossing directions for droplet merging and mixing.

There is a still another method of droplet transfer in which a small volume droplet is transferred being placed on a different member. In an example application of such a method (disclosed in JP-A No. 271185/1999), a liquid is scooped with a hydrophobic-surfaced ring included in a transfer member, and the liquid scooped and spherically formed by its surface tension is transferred being held on the ring of the transfer member. In a still another method (disclosed in JP-A No. 509274/2002), a ring-shaped member included in a device for depositing a liquid dot on a surface holds liquid formed like a film, the liquid is pricked with a pin, and the liquid dot formed on the pin is deposited on a surface.

SUMMARY OF THE INVENTION

The problems to be solved by the present invention include the following. First, of the above conventional techniques, the methods in which a flow path or a plane are utilized have the following problems. When a liquid comes in contact with a wall, it contaminates the wall thereby changing the surface properties of the wall. The accuracy in controlling the behavior and size of a droplet to transfer, the repeatability of movement behavior, the efficiency of final chemical reactions, and the accuracy of final analysis are degraded, respectively. It is also problematic that the subsequent droplets to be transferred are possibly contaminated, too. Such droplet contamination possibly degrades chemical reactions, and analysis and inspection accuracy. Preparing a flow path and a plane required to transfer a droplet involves high cost. Particularly, it takes a high cost to form a surface provided with a fine flow path and electrodes. Hence, it is difficult to make such parts disposable to avoid contamination problems. As a solution in these regards, it may be considered to clean such parts after use and use them again. Generally, however, there is a limitation in recovering surface properties of used parts by cleaning. When flat electrodes are used for droplet transfer, it is necessary to change the electrode arrangement according to the size of droplets to be transferred. In other words, an electrode arrangement is good for droplets not largely differing in size. The surface properties of parts to come in contact with droplets largely affect the transfer of the droplets, but achieving uniform surface property repeatability is difficult. This results in difficulty in achieving high droplet size accuracy. Furthermore, it is difficult to transfer droplets for which electrical means cannot be used or droplets with a heavily contaminated surface. Hence, it is necessary to take into consideration the kinds of liquids to be transferred as droplets.

The methods in which droplets are transferred in air have a problem in that the size of droplets which can be transferred is limited. When a droplet with a weight exceeding a certain limit is made to fly for a transfer, it falls by gravity earlier than expected. As no wall is erected in the air where these methods are used, contamination problems are not serious, but these methods in which droplets cannot stay long in the air are not suitable in cases where slow chemical reactions are to be analyzed and inspected.

The methods in which a flow path and a plane are used or in which droplets are transferred in the air all have a problem in that, as the number of droplets to be transferred increases, it becomes necessary to use a complicated device structure. This makes creating and operating a required device difficult and increases equipment cost. Furthermore, it is necessary to modify the device structure every time the number of droplets to be transferred changes.

The other methods also introduced as conventional techniques above have a problem, particularly, as to the size of droplets which can be handled. For example, the maximum volume of a droplet that can be transferred by the droplet transfer method disclosed in JP-A No. 271185/1999 is considered to be about 19 microliters according to calculations made, based on a maximum ring radius of 0.8 mm, by using an expression given in the present specification. Also, the droplet holder used in the method disclosed in JP-A No. 509274/2002 holds a liquid film with a surface diameter of 0.375 micron or less, and the pin with which to prick the liquid film is considered to be smaller than the liquid film.

With such a configuration, it is not possible to transfer a liquid volume of 1 microliter or more. It is also problematic that the method, while having a droplet size limitation, requires the configuration to be changed to handle droplets of different sizes. Furthermore, with these methods, it is difficult to perform droplet merging, mixing, and dripping.

The measures taken by the present invention to solve the above problems are as follows. In a simplest configuration, an annular droplet holder formed of wire is used to hold a droplet. Unlike for the droplet transfer method disclosed in JP-A No. 271185/1999, the droplet holder need not necessarily be hydrophobic. It can therefore be formed easily and inexpensively by using a general hydrophilic metallic wire. A droplet is held by the droplet holder in a state of hanging from the annular wire. The droplet being held remains stable. For example, when the droplet volume changes, the droplet can easily withstand the change as its surface tension allows it to change its shape correspondingly. To realize a droplet transfer, the annular droplet holder is attached with a means for moving the droplet holder. For example, when the annular droplet holder is attached with a handle including an upwardly extending wire connected to a stage, the droplet held by the droplet holder can be transferred by moving the stage.

The droplet transfer method according to the present invention imposes no significant restrictions on the droplet holder material, and it uses a simple, inexpensive, easy-to-replace configuration. It is also an advantage of the present invention that, unlike in the case of the method in which a flow path or a plane is used for a droplet transfer, the part to come in contact with liquid can be easily cleaned. When a flow path or a plane is used for a droplet transfer, the entire flow path or plane is subjected to contamination. In the case of the present invention, on the other hand, the surface area to come into contact with liquid is limited to the droplet holder, so that the surface area to come into contact with liquid is much smaller than in the case of the method in which a flow path or a plane is used. Thus, whether to depend on part replacement or part cleaning, it is easy to cope with contamination problems according to the present invention. Generally, when a method in which a flow path or a plane is used for a droplet transfer, the same flow path or plane is passed by different kinds of fluids. The present invention, on the other hand, allows wires and their surface properties to be appropriately selected according to the kinds of fluids to be transferred. This makes it possible to improve droplet size accuracy and transfer repeatability. According to the present invention, a droplet can be stably held and transferred taking an adequate amount of time. Therefore, unlike in the case of the methods in which droplets are made to fly for a transfer, no problem associated with a limited transfer time arises.

Even when the number of droplets to be transferred increases, the change can be coped with by simply increasing the number of droplet holders. The configuration used by the droplet transfer method of the present invention is simple, so that it can be created and operated with ease without involving a large cost increase. When the number of droplets to be transferred changes, the number of droplet holders can also be changed correspondingly. Using the configuration, a droplet of about 20 microliters or more can be easily transferred. The configuration also allows as small a droplet as 1 nanoliter to be transferred.

As for droplet mixing, moving the droplet holder up and down or side to side changes the droplet shape generating a liquid flow inside the droplet. Thus, the inside of the droplet can be easily agitated. It is also possible to insert a wire rod into the droplet held by the droplet holder and agitate the inside of the droplet. Vibrating the droplet using a vibrator is also effective.

Bringing the droplets held by droplet holders into contact easily merge the droplets. When the droplets are merged, a flow is generated in the liquid in the merged droplet, so that the liquid in the merged droplet is agitated automatically. Between two droplets of different sizes, the smaller one has a larger internal pressure according to Laplace's law. Therefore, a manner of droplet merging in which the smaller one of two droplets is absorbed by the larger one can be steadily repeated. It is also possible to merge, with ease, two droplets by vertically moving the larger one of the two until coming into contact with the smaller one or by using non-annular droplet holders being described in the following.

It is possible, by using an external force, to deform a droplet holder formed of wire and thereby reduce the droplet holding power of the droplet holder to remove the droplet held by the droplet holder, that is, to drip the droplet onto a prescribed location. The droplet can also be transferred to a prescribed location by moving it to the location until coming in touch with the location.

Another simple shape of a droplet holder is a spiral shape. A spiral droplet holder can hold liquid in its portion with a small spiral pitch. When its spiral pitch is larger than a certain value, it cannot hold liquid. An advantage of a spiral droplet holder is that, whereas scooping liquid is difficult with an annular droplet holder, a spiral droplet holder can scoop liquid with ease. A spiral droplet holder is compatible with a large volume of liquid. A prescribed amount of liquid can be scooped by immersing a spiral droplet holder in liquid and then lifting it up. Part or whole of the liquid held by a spiral droplet holder can be dripped onto a prescribed location by widening the spiral pitch of the spiral droplet holder. The spiral pitch of the spiral droplet holder can be widened, for example, by pulling an end of the spiral forming wire with an appropriate part. When the spiral droplet holder is formed of a shape-memory alloy, it can be straightened by appropriately changing its temperature.

Droplet transfer by use of an annular or spiral droplet holder formed of wire has been described, but the droplet holder can be other than annular or spiral. Its shape can be appropriately changed, for example, according to the size and kind of the droplet to be transferred or the purpose of droplet reaction analysis to be performed. Compared with cases where a droplet is held and dripped using a pipette, using the droplet holders as described above is advantageous in that it does not require such additional parts as a piston. Another advantage is that the droplet holders enable multiple droplets to be concurrently handled.

The configuration described above of the method according to the present invention can be used for droplet holding, merging, mixing, agitation, and extended retention besides it can be easily expanded, too. It can therefore be used to form small volume droplets and to create chemical reactions using droplets. Furthermore, it can also be used in the fields of chemical analysis, biochemical analysis, and automatic blood analysis to be conducted using liquid droplets. Concrete examples to which the method according to the present invention can be applied include spectroscopic cells used for absorbance measurement.

The present invention enables inexpensive, simple droplet transfer. The present invention also makes it possible to perform droplet agitation, merging, mixing, and dripping with ease. Hence, an inexpensive, simple configuration for handling droplets in the fields of chemical analysis, biochemical analysis, and automatic blood analysis can be realized according to the present invention. For applications requiring contamination to be taken into consideration, the present invention allows parts which come into contact with liquid to be made disposable to avoid contamination problems. When the present invention is applied to inspection work, the cost of inspection can be held low. The present invention can easily cope with changes in the size and number of droplets to be transferred. It is possible to create a large number of uniform small volume droplets. When applied to spectroscopic cells, the present invention enables measurement based on a very small amount of liquid, so that the light path used for measurement can be made shorter than when the present invention is not applied. When the present invention is applied, the sample used in measurement can be recovered.

BRIEF DESCRIPTION OF THE DRAWINGS

FIG. 1 is a schematic diagram showing a droplet transfer method according to an embodiment of the present invention;

FIGS. 7A to 7H are schematic diagrams showing a series of operations leading from droplet holding to droplet transfer and droplet dripping according to an embodiment of the present invention;

FIGS. 8A and 8B are schematic diagrams showing a method of droplet dripping according to an embodiment of the present invention;

DETAILED DESCRIPTION OF THE PREFERRED EMBODIMENTS

Figure 2A:
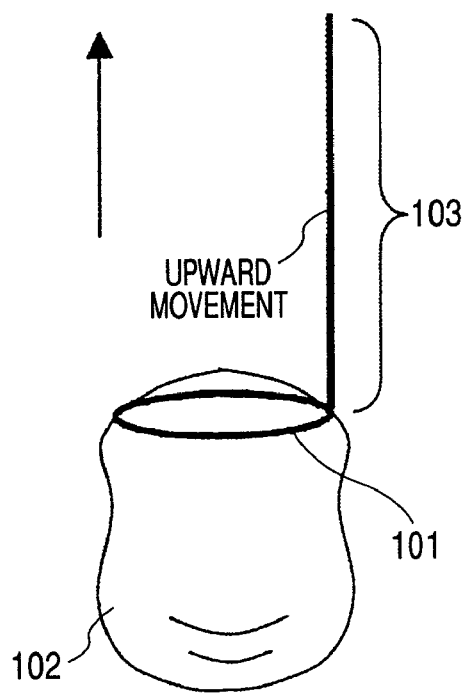
FIGS. 2A and 2B are schematic diagrams showing droplet agitation according to an embodiment of the present invention.

In the following, embodiments of the present invention will be described with reference to the accompanying drawings. FIG. 1 is a schematic diagram of the droplet transfer unit according to an embodiment of the present invention. An annular droplet holder 101 holding a droplet 102 is attached with a transfer handle (transfer unit) 103. Both the annular droplet holder 101 and the handle 103 are formed of wire. The droplet 102 is held by the annular droplet holder 101. It is, as viewed macroscopically, inscribed in the annular droplet holder 101 while resisting gravity by virtue of its surface tension and thereby maintaining its shape. The droplet 102 is kept nearly spherical by its surface tension, and is held by the annular droplet holder in a manner of being hung therefrom. An annular droplet holder having a diameter (inscribed diameter) of about 2.7 mm and being made of a stainless wire with a diameter of 100 microns, for example, can hold a water droplet of about 50 microliters. Similarly, a droplet holder having a diameter of about 3.2 mm and being made of a solder wire with a diameter of about 0.5 mm can hold a droplet of about 75 microliters. Thus, the volume of water held by an annular droplet holder can be adjusted by changing the diameter of the droplet holder, and the diameter and surface properties of the wire making up the droplet holder. A droplet holder is capable of holding a droplet ranging in volume from 10 nanoliters to several hundred microliters.

The volume of a droplet that can be held by a droplet holder can be approximately estimated as follows. When, without changing the shape and size of the annular droplet holder 101, the volume of the droplet 102 held by the droplet holder 101 in a state of being inscribed therein is gradually increased, the droplet 102 initially shaped spherically changes its shape to be slightly constricted in a portion below the droplet holder 101 before finally falling from the droplet holder 101. In the present embodiment, the handle 103 is positioned higher than the annular droplet holder 101, so that it does not interfere with the formation of a droplet. A droplet can be stably held by the annular droplet holder only while the surface tension applied to the inscribed circumference, having an inscribed diameter, of the droplet holder can support the total weight of the droplet. When the largest droplet that can be stably held by the droplet holder is approximated by a sphere with a volume V and a diameter D, the following equation can be obtained: $2\pi d \times \gamma = V \times \rho \times g = (\pi/6) \times D3 \times \rho \times g$, where d represents an inscribed diameter, $\gamma$ a surface tension, $\rho$ a liquid density, and g a gravitational acceleration. When inscribed diameters of 2.7 mm and 3.2 mm, the same values as used in the above experiment, are assigned to the equation together with water property values, the droplet volume V is approximated as 63 and 75 microliters, respectively. Of the two approximated values, while the former associated with the thinner wire is a little smaller than the experimentally obtained corresponding value possibly due to a stability-related problem, the latter associated with the thicker wire exactly matches the experimentally obtained corresponding value. A limitation to the present method of holding a droplet is where the values of D and d become equal, that is, d=D=6.7 mm. It is certainly possible to control the inside diameter of an annular droplet holder in a range of about 10 microns to 6.7 mm. Based on this, the volume of the droplet held by the droplet holder is calculated to range from 23 nanoliters to 156 microliters. These are the lower limit droplet volumes according to calculations that can be held by the droplet holder with the above range of an inside diameter. In reality, it is possible, using a droplet holder with the above range of an inside diameter, to hold a droplet of a smaller volume. On the higher limit side, changing the droplet holder shape from a true annular shape to an elliptical annular shape can increase the droplet volume that can be held by the droplet holder. Using an elliptical droplet holder makes it possible to hold and transfer a droplet ranging in volume from 10 nanoliters to a sub-milliliter. When using an annular droplet holder with a diameter of 1 mm, it is possible to hold and transfer a droplet of about 20 microliters.

The droplet 102 held by the droplet holder 101 can be transferred as desired by three-dimensionally moving the transfer handle 103 attached to the droplet holder 101. There are many ways of three-dimensionally moving the transfer handle 103. For example, a mechanical arm designed to grasp and move the transfer handle may be used, or a method using an xyz stage may be adopted. A droplet can be three-dimensionally transferred stably by controlling the transfer speed so as not to allow the droplet to fall while being transferred. Even though, in the schematic diagram of FIG. 1, the droplet holder is shown in a horizontal position, it need not necessarily be kept horizontal. It can hold and transfer a droplet even in an inclined position.

Figure 2B:
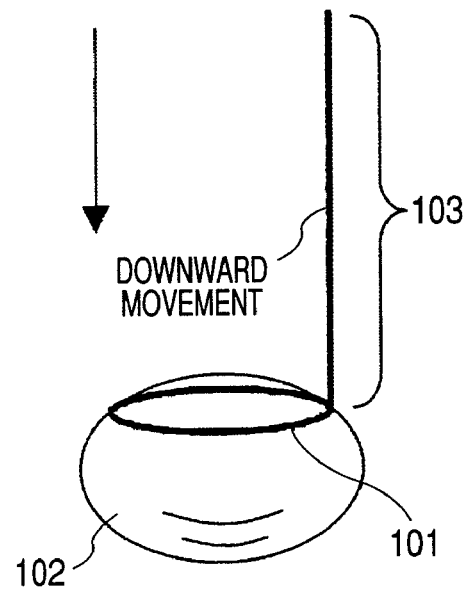

FIGS. 2A and 2B are schematic diagrams showing droplet agitation. Holding the handle 103 described with reference to FIG. 1 and moving it up and down generates the states as shown in FIGS. 2A and 2B alternately, causing the liquid contained in the droplet to internally move to be thereby agitated. The force to hold the droplet 102 of the annular droplet holder 101 is large enough not to allow the droplet 102 to fall even when the droplet holder 102 is jiggled up and down. This method of agitation is remarkably effective when the droplet to be agitated is relatively large, say, larger than 10 microliters in volume. When the droplet to be agitated is smaller than that, the effect of molecular effect in the droplet is large enough, so that, in many cases, agitation is not necessary. Even though FIGS. 2A and 2B show droplet agitation by up and down movement, lateral or rotational movement can generate a similar agitation effect.

Figure 3A:
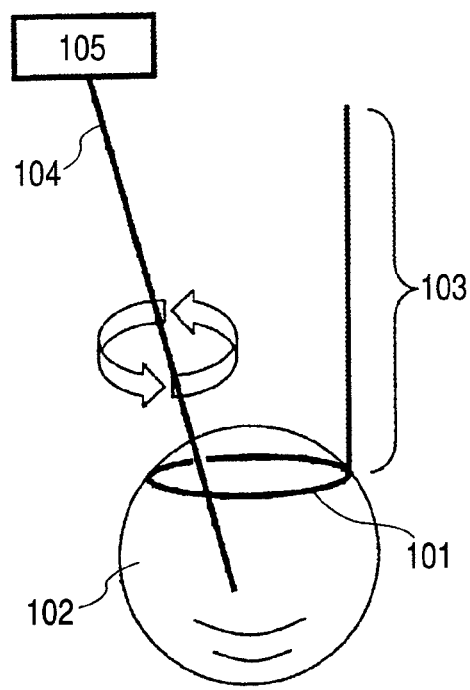
FIGS. 3A and 3B are schematic diagrams showing droplet agitation according to an embodiment of the present invention.
Figure 3B:
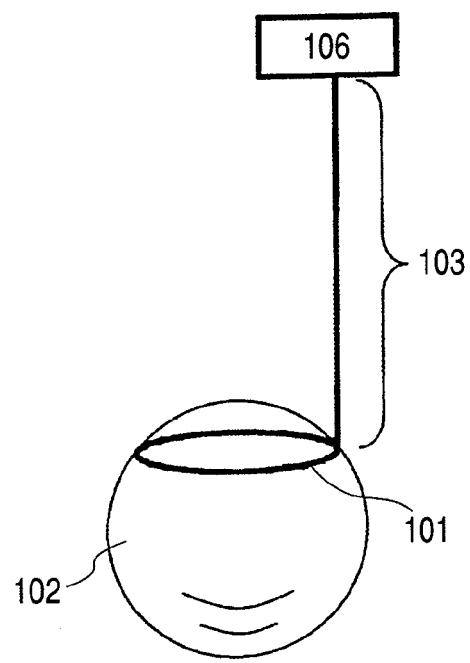

FIGS. 3A and 3B are schematic diagrams showing droplet agitation performed by methods different from that shown in FIGS. 2A and 2B. The schematic diagram of FIG. 3A shows an agitation method in which a stirring rod is used. An end of a stirring rod 104 which can penetrate through the inside of the annular droplet holder 101 is inserted into the droplet 102 with the other end of the stirring rod 104 connected to a stirring motor 105. The droplet is mechanically stirred using the stirring motor for agitation. The schematic diagram of FIG. 3B shows an agitation method in which vibrations are used. An eccentric motor 106 is connected to the handle 103 and vibrates the handle 103 to agitate the droplet 102 via the droplet holder 101. Even though, in the methods shown in FIGS. 3A and 3B, a motor is used as a means for agitation or vibration, the methods do not necessarily require the use of a motor.

Figure 4A:
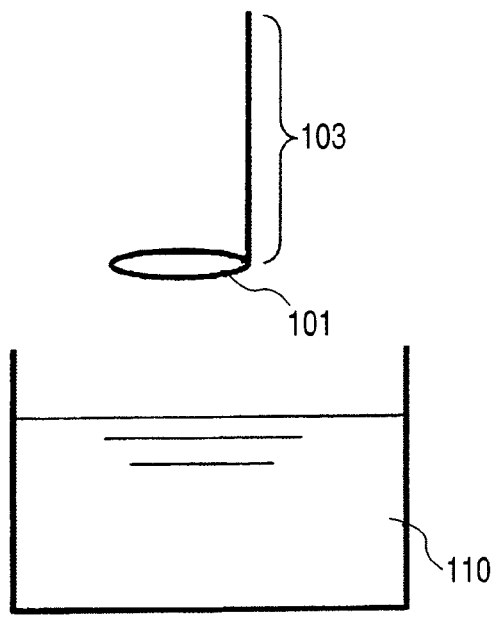
FIGS. 4A to 4D are schematic diagrams showing a method of forming a droplet on a droplet holder according to an embodiment of the present invention.
Figure 4B:
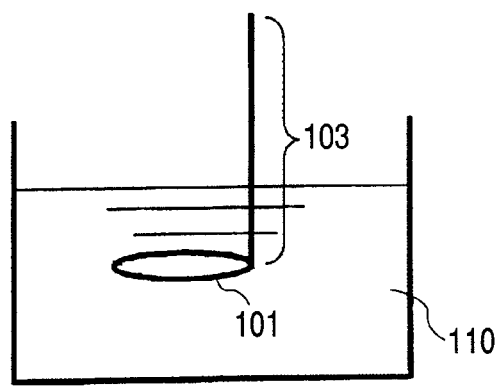
Figure 4C:
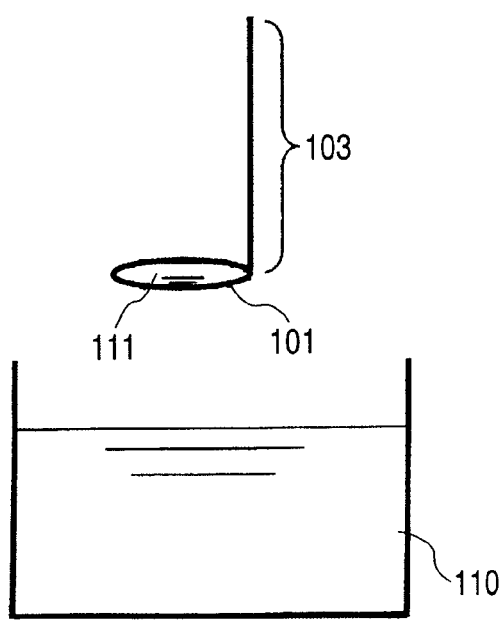
Figure 4D:
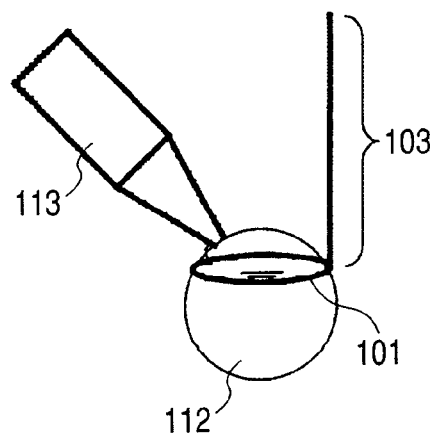

FIGS. 4A to 4D are schematic diagrams showing a method of forming a droplet on a droplet holder. First, as shown in FIG. 4B, the droplet holder 101 is immersed, using the handle 103, in the target liquid contained in a container 110. Next, as shown in FIG. 4C, the droplet holder 101 is lifted using the handle 103. At this time, no spherical droplet forms at the droplet holder 101, but a liquid film 111 forms. Finally, as shown in FIG. 4D, a solution is added to the liquid film 111 using a liquid supply means 113 (for example, a pipette). As the solution is added, a droplet 112 is formed at the droplet holder 101 such that it has a gravity center in its lower portion and such that it is convex mainly downwardly while also convex upwardly. This can be achieved in a stable state without requiring any particular care to be used when adding the solution to the liquid film 111 by the use of the liquid supply means 113. Dripping the solution onto the liquid film 111 from an appropriate height is allowable. Or, it is also allowable to bring the tip of the liquid supply means 113 into contact with the liquid film 111 and, in that state, push the solution out of the liquid supply means 113. The method of forming a droplet on the droplet holder is not limited to the above-described. For example, in cases where a droplet to be held on the annular droplet holder is as large as or larger than the droplet holder, the droplet can be placed on the droplet holder directly from the liquid supply means. There are also cases in which a droplet is formed on the joint between the handle 103 and the droplet holder 101 and then a solution is added to the droplet from the liquid supply means causing the droplet to grow into an appropriate size. It is difficult to apply these methods of forming a droplet on a droplet holder, for example, in a case where liquid is put on an end of a pin included in a device configuration used to deposit a fluid dot on a surface as described in JP-A No. 509274/2002. The applicability of these droplet forming methods is an advantage of using a droplet transfer unit shaped according to the present invention. The droplet held by a droplet holder can be destroyed by blowing it off with a gas, for example, air using a gas supply means. This makes it possible to use the droplet holder a plural number of times.

Figure 5C:
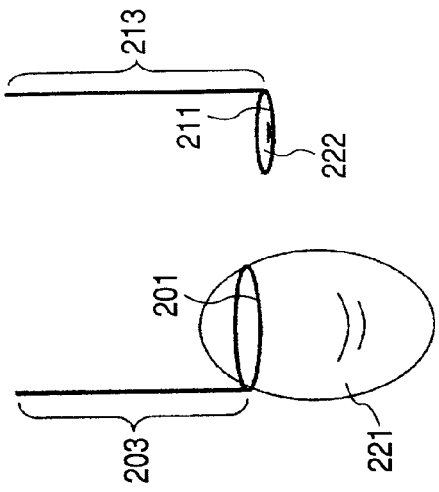
FIGS. 5A, 5B, and 5C are schematic diagrams showing droplet mixing according to an embodiment of the present invention.
Figure 5A:
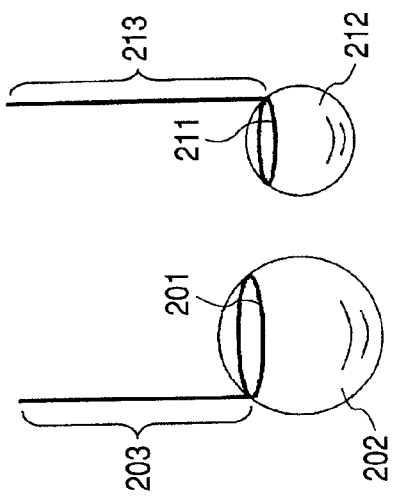
Figure 5B:
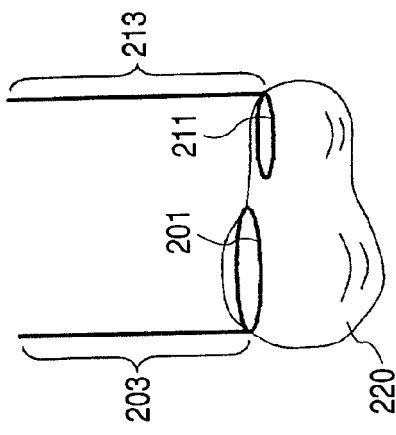

FIGS. 5A, 5B, and 5C are schematic diagrams showing droplet mixing in which two droplets of different sizes are mixed by using plural droplet transfer units including annular droplet holders with different diameters. FIG. 5A shows two droplets in a state before being mixed. A larger droplet 202 shown on the left is held by an annular droplet holder 201 in a state in which it is transferable using a handle 203. A smaller droplet 212 shown on the right is held by an annular droplet holder 211 in a state in which it is transferable using a handle 213. The annular droplet holder 201 has a larger diameter than the annual droplet holder 211. FIG. 5B shows a state in which the two droplets have been brought into contact to form a mixed droplet 220. The mixed droplet 220 is held in a state of hanging from the two annular droplet holders 201 and 211. FIG. 5C shows a state in which the mixed droplet 221 has been transferred to the annular droplet holder 201 by moving the handles 203 and 213 that were close to each other in the state shown in FIG. 5B away from each other. Almost no liquid is left on the smaller annular droplet holder 211. There is only a liquid film 222 left on the droplet holder 211. Even the liquid film 222 is not necessarily left there. For, depending on the angle of direction in which the two annular droplet holders 201 and 211 are moved away from each other and the relative speed at which they are moved away from each other, the droplet 221 can be completely transferred to the droplet holder 201 without causing formation of the liquid film 222. Another method may be used in which, when the two annular droplet holders 201 and 211 are moved away from each other, the liquid film 222 is pricked with a pin to cause the liquid film 222 to be ruptured and completely transferred to the droplet holder 201. Thus, the two droplets can be mixed and transferred to one of the two droplet holders. Of the two droplets, the one with a smaller curvature has a higher internal pressure due to the Laplace pressure effect. In a case where, as in the present embodiment, two droplets are laterally brought into contact, they are merged in a manner in which the smaller droplet is absorbed by the larger droplet. It is also possible to mix, with ease, the two droplets in a different manner in which the larger droplet is joined to the smaller droplet, for example, by vertically bringing the two droplets into contact or by using non-annular droplet holders being described in the following.

Figure 6:
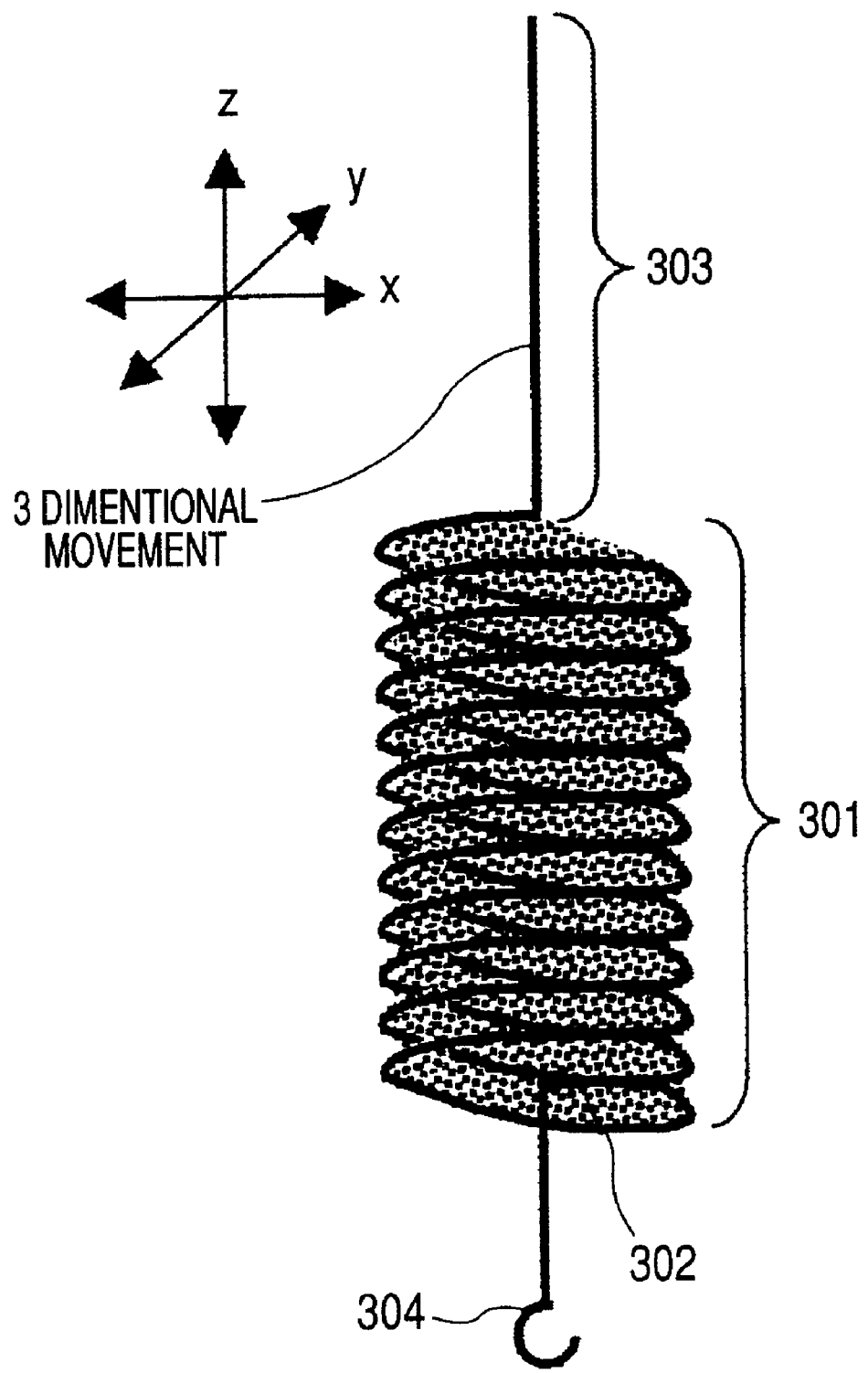
FIG. 6 is a schematic diagram showing droplet transfer according to an embodiment of the present invention.

FIG. 6 is a schematic diagram showing a second embodiment of the droplet transfer unit according to the present invention. In this embodiment, a spiral droplet holder different from the annular droplet holders used in the foregoing embodiment is used. A spiral droplet holder 301 is attached with a transfer handle 303. The droplet holder 301 and the handle 303 are both made of wire. A droplet 302 is held by the spiral droplet holder 301. The droplet 302 is, as viewed macroscopically, inscribed in the spiral droplet holder 301 while resisting gravity by virtue of its surface tension and thereby maintaining its shape. The droplet 302 is almost spirally shaped being inscribed, as viewed macroscopically, in the droplet holder 301. When, unlike in cases in which a droplet is hung from an annular droplet holder, a droplet is held along the whole length of the spiral droplet holder 301, the volume of the droplet being held is almost constant. The volume V of the droplet roughly coincides with the inside volume of the spiral droplet holder. The volume V can be virtually expressed by the equation: $V=\pi d^2/4 \times p \times n$, where n represents the number of turns of the spiral, d the spiral diameter, and p the spiral pitch. Appropriately varying the variables of the expression makes it possible to design a droplet holder for holding a droplet of a desired volume. A spiral droplet holder can hold a droplet which is as large as or larger than the volume of a droplet held by the annular droplet holder of the foregoing embodiment. A projection 304 at a lower end portion of the spiral droplet holder 301 is not indispensable in transferring a droplet, but it is effective when releasing a droplet as being described later. Like in the first embodiment, the droplet 302 held by the droplet holder 301 can be transferred in arbitrary directions by three-dimensionally moving the transfer handle 303. In terms of the droplet stability during transfer, the spiral droplet holder is superior to the annular holder, so that it enables stable transfer.

FIGS. 7A to 7H are schematic diagrams showing a series of operation leading from droplet holding to droplet transfer and droplet dripping. FIG. 7A shows a state in which no droplet is held by the droplet holder 301 and the solution to be transferred is contained in a container 310. FIG. 7B shows a state in which the droplet holder 301 is immersed in the solution contained in the container 310. When the droplet holder 301 is immersed in the solution contained in the container 310 using the transfer handle 303, the solution enters the inside of the droplet holder 301. Even though, in the state shown in FIG. 7B, the spiral droplet holder 301 is entirely immersed in the solution, the depth up to which the droplet holder 301 is to be immersed in the solution may be controlled so as to immerse the spiral droplet holder 301 only partly in the solution and have a droplet of a desired volume held by the droplet holder 301. FIG. 7C shows a state in which the droplet holder has been lifted out of the solution. When the droplet holder 301 is lifted out of the solution, the droplet 302 is held only inside the spiral droplet holder 301; it is held at no other parts of the spiral droplet holder 301. FIG. 7D shows a state in which the droplet 302 is being transferred. The droplet 302 can be transferred to a desired location using the handle 303. FIG. 7E is a schematic diagram showing a state in which the droplet 302 has been transferred to above a transfer destination, that is, a well 311 on a microplate. The arrangement shown in the schematic diagram of FIG. 7E includes a projection 312 projecting at a bottom portion of the well 311. After this state is reached, the droplet holder 301 is lowered to drip the droplet 302 into the well 311 on the microplate. FIG. 7F is a schematic diagram showing a state in which the projection 304 located below the droplet 302 is hooked to the projection 312 in the well 311 on the microplate. FIG. 7G is a schematic diagram showing a state in which the droplet 302 has been dripped into the well 311 on the microplate by lifting the handle 303 with the projections 304 and 312 hooked to each other. When the spiral droplet holder 301 is stretched, the spiral pitch expands causing the droplet 302 that has been held by the surface tension of the liquid to drip by gravity into the well 311 on the microplate where it is kept as a liquid 313. FIG. 7H shows a state in which the spiral droplet holder 301 has been lifted to a previous position after the projections 304 and 312 were released from each other. Going through the steps shown in FIGS. 7A to 7H makes it possible to form a droplet out of the solution contained in a container and transfer the droplet to a prescribed location. In the present embodiment, the spiral droplet holder 301 is stretched with the projection 304 provided below it hooked to the projection 312 provided on the well 311, but the present invention is not limited to the method. For example, a droplet can be dripped by such a simple method in which an end portion of the droplet holder is pinched and pulled down with something like tweezers. A method in which a shape-memory alloy is used as in the embodiment being described next is also effective.

FIGS. 8A and 8B are schematic diagrams showing a method of droplet dripping according to a third embodiment of the present invention. FIG. 8A is a schematic diagram showing a state in which a droplet 402 held by a spiral droplet holder 401 formed of a shape-memory alloy is about to be dripped. To have a droplet formed on the droplet holder, the method of the second embodiment may be used, or the method of the first embodiment in which liquid is placed on a droplet holder using a liquid supply means may be used. A heater 404 connected to a controller 405 is attached to a handle 403 to control the temperature of the spiral droplet holder 401. When, in the state shown in FIG. 8A, the controller 405 is operated to turn the heater 404 on, the spiral droplet holder 401 is stretched into a wire 407 as shown in FIG. 8B. Since the wire 407 cannot hold the droplet 402, the droplet 402 drips onto the bottom of a test tube 406. This arrangement can be made by using a spiral droplet holder made of a shape-memory alloy remembering a linear shape. To mitigate problems of evaporation or denaturation possibly caused when the solution is heated, a shape-memory alloy having a shape-memory temperature of, for example, 30 to 40° C. may be used. Even though, in FIG. 8B, the spiral droplet holder is shown having been stretched into a straight wire, it does not necessarily require to be completely straightened. In the present embodiment, to reduce the possibility of the droplet 402 splashing onto different locations thereby soiling such locations when the spiral droplet holder 401 is transformed into a straight wire, the spiral droplet holder 401 is heated inside the tall test tube 406. The possibility can also be reduced by giving attention to the direction along which a shape-memory alloy wire is spiraled to form the spiral droplet holder 401. A method in which, before the droplet 402 is dripped, another wire is inserted in the spiral droplet holder 401 so that the droplet 402 flows down to a prescribed location along the inserted wire is also effective. Compared with the foregoing method in which a droplet holder is hooked to a projection provided on a plate or in which something like pliers are used to stretch a droplet holder, the present embodiment in which a shape memory alloy is used is advantageous in that it requires no projection to be provided on the plate and in that it is less likely to involve contamination problems, for example, attributable to the use of pliers.

Figure 9A:
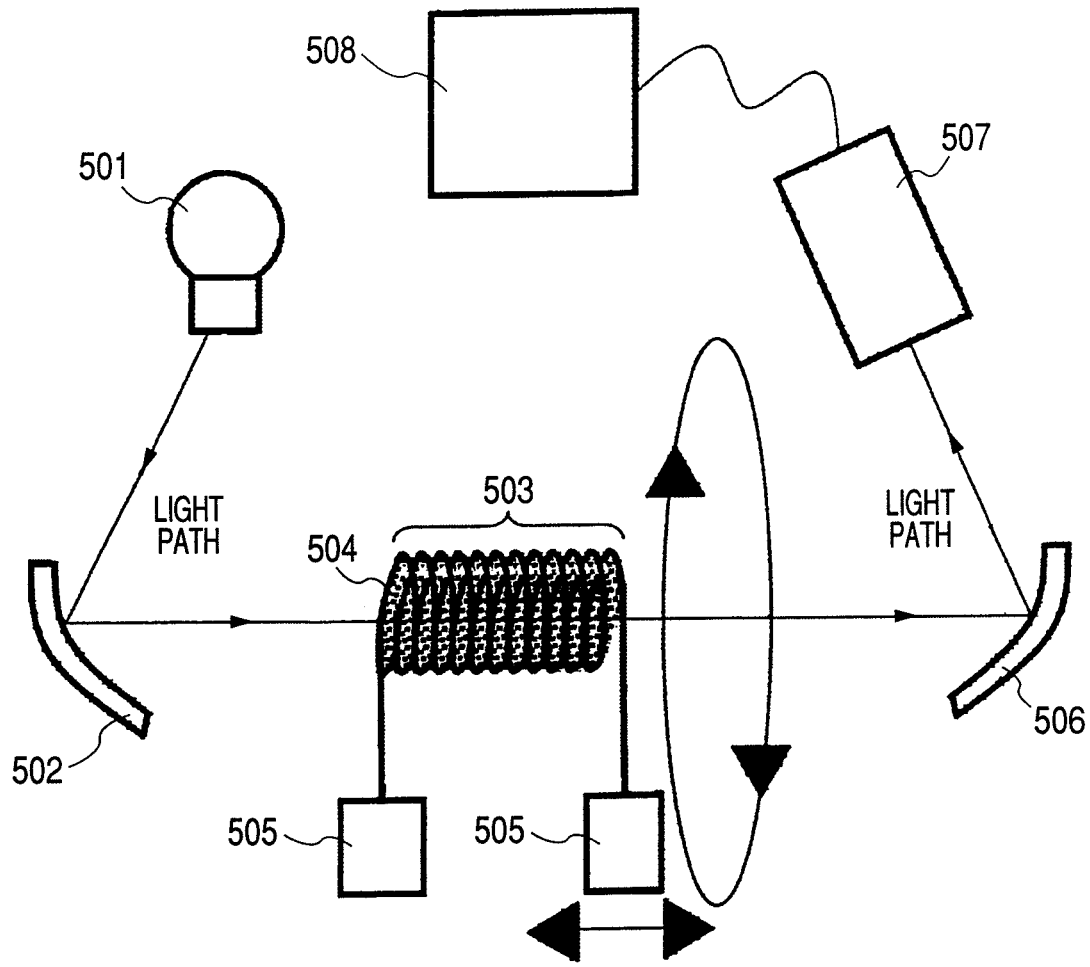
FIGS. 9A and 9B are schematic diagrams showing an optical measurement apparatus according to an embodiment of the present invention.
Figure 9B:
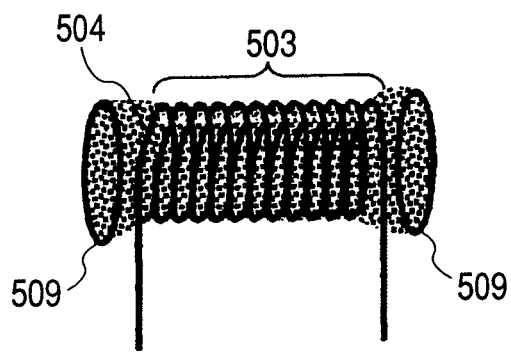

FIGS. 9A and 9B are schematic diagrams showing an optical measurement apparatus according to a fourth embodiment of the present invention. In this embodiment, a spiral droplet holder is utilized also as a spectroscopic cell. Even though the spiral droplet holder is applied to an absorption spectrophotometer in the present embodiment, it may be applied to a different kind of analysis equipment. FIG. 9A is a schematic diagram showing principal parts of the absorption spectrophotometer according to the fourth embodiment of the present invention. Light emitted from a lamp 501 passes, after being reflected by a mirror 502, through the inside of a spiral droplet holder 503 holding a target solution droplet 504. The length of the droplet holder 503 defines the light path length L of the absorption spectrophotometer. A pair of supports 505 provided to adjust the length of the droplet holder 503 are rotatable and capable of adjusting the distance between them. The supports 505 are not indispensable in performing absorbance measurement, but they can play important roles in arranging operational conditions for absorbance measurement on a small volume droplet. The light having passed the solution droplet 504 undergoes wavelength dispersion at a diffraction grating 506. Subsequently, the light is received by a photomultiplier tube 507 connected to a data processor 508. The absorbance of a solution can be measured using the above configuration. Usually, for measurement using an absorption spectrophotometer, a solution to be measured is put in a quartz or plastic cell of the absorption spectrophotometer through an open top portion of the cell. In many cases, therefore, the light path in the absorption section of the absorption spectrophotometer is substantially horizontal. In the configuration of the present embodiment, too, the light path is substantially horizontal, so that the axis of the spiral droplet holder is also substantially horizontal. In such an arrangement, too, the droplet 504 can be held stably.

Absorbance measurement on a small volume droplet which used to be difficult to carry out can be performed with ease by the above method. The above method also makes it possible to recover used solution or use disposable spectroscopic cells. Assume, for example, absorption spectrometry is to be performed using a microliter of liquid. Also assume that the droplet holder to be used has a 10-turn spiral formed by spiraling a stainless steel wire with a diameter of 125 microns such that the inside diameter of the spiral is 1 mm with mutually adjacent spiral turns in firm contact with no spacing between them. The length of the spiral is given as 'L=125 microns×n (=10)=1.25 mm', and the inside volume of the spiral is given as 'V=($\pi d^2/4$)×L=(3.14×1 [mm]$^2$/4)×1.25 [mm]=0.98 [mm$^3$]', respectively, where d represents the inside diameter of the spiral, L (same as the light path length) the length of the spiral, n the number of spiral turns, and l the length of the wire forming the spiral. The inside volume of the spiral is approximately 1 microliter. In cases where absorbance measurement is performed on nucleic acid or protein, recovering the solution after use is important. The target solution in such cases is most likely an aqueous solution, and a spiral of a hydrophilic metal wire will effectively hold a droplet of the solution. It is also possible to use a spiral of a resin wire with improved surface quality. In fact, with no spacing between spiral turns, no substantial problem will arise. The wire length l is approximately given as 'l=$\pi$dn=3.14×1 mm×10=31.4 mm'. Thus, the required wire length is very short, so that it is possible to prepare inexpensive spectroscopic cells and use them as disposable cells. This enables contamination-free absorbance measurement. In cases where the solution contains an adequately high concentration of target molecules, the light path length of 1.25 mm will be enough to measure the absorbance of the molecules. When the concentration is not adequately high, however, it is necessary to lengthen the light path. In such a case, the light path length can be increased from 1.25 mm to 5 mm by adjusting the distance between the pair of supports 505. To keep the diameter of the spiral unchanged so as to keep the inside volume of the spiral unchanged, it is known based on calculations that the number n of spiral turns requires to be increased from 10 to 20. After such changes are made, the diameter of the spiral is about 500 microns, and the spacing between spiral turns is about 250 microns. The target solution is kept adequately stable during measurement. If a spiral with a smaller diameter is formed using a thinner wire, absorbance measurement on a smaller droplet is enabled. Even though, on account of the meniscus on the droplet surface, the light path becomes slightly shorter than the length of the spiral droplet holder, such an error in the light path length is not significant in general absorbance measurement. If, based on the droplet composition, the meniscus on the droplet surface is taken into account in a design stage, it is possible to secure an accurate light path length. An accurate light path length can also be secured by another method in which, as shown in FIG. 9B, a pair of members 509 made of substantially transparent material such as glass are disposed on both sides of the droplet holder 504 thereby forming a liquid bridge between each of the pair of members 509 and the droplet holder 504. The pair of members 509 is effective whether they are flat or curved like a lens. Providing each of the pair of members 509 with a curved surface like a lens so that it collects external light and so that the collected light penetrates efficiently and accurately through the inside of the droplet is also an effective method.

Figure 10A:
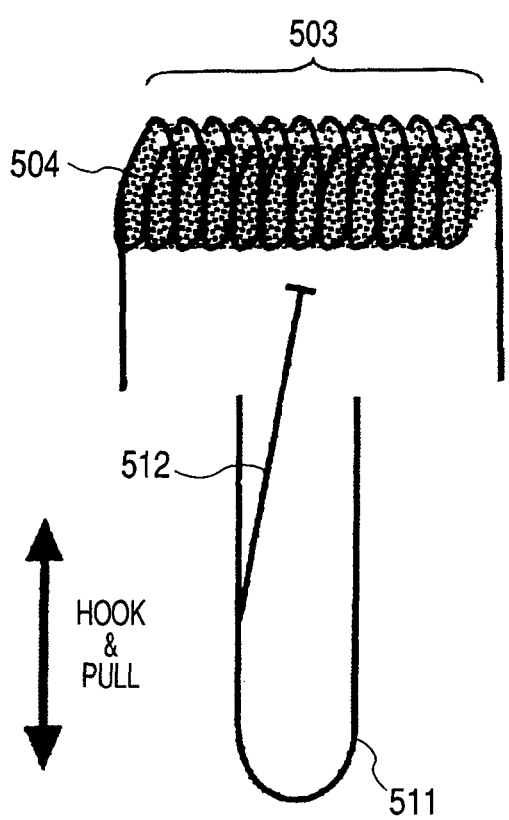
FIGS. 10A and 10B are schematic diagrams showing a droplet recovery method according to an embodiment of the present invention.
Figure 10B:
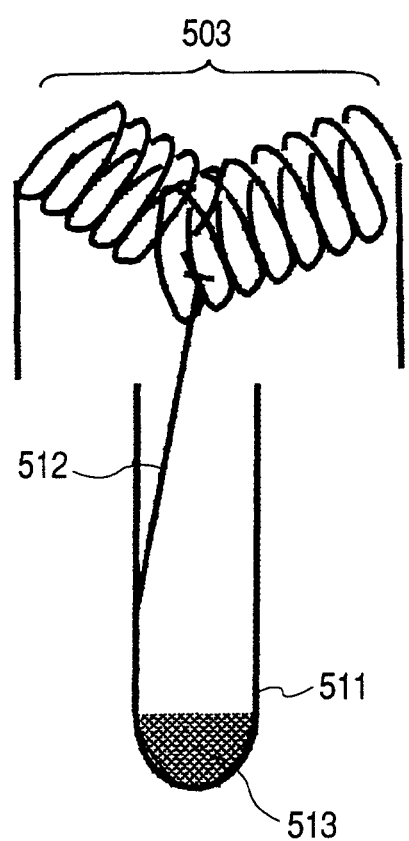

FIGS. 10A and 10B are schematic diagrams showing a droplet recovery method according to the fourth embodiment of the present invention. A projection 512 projecting from a container 511 is hooked to a substantially middle portion, or to its vicinity, of the spiral droplet holder 503 holding the droplet 504. In this state, pulling the projection 512 deforms the spiral droplet holder 503 causing the droplet 504 to drip into the container 511. The droplet 504 having dripped into the container 511 is recovered as a solution 513. Like in this case, the direction in which the droplet holder 503 is deformed need not be the same as the axial direction of the spiral. The projection 512 is preferably linear and extends upward in a direction not largely deviating from vertical, so that liquid can smoothly flow down along the projection 512. This arrangement for droplet recovery can be incorporated in an absorption spectrophotometer. Alternatively, the droplet holder may be removed from the absorption spectrophotometer and the above recovery method may be manually performed. Using the droplet holder as a spectroscopic cell enables the solution used in absorbance measurement to be recovered with ease. In absorbance measurement generally performed using, for example, a quartz cell, the solution after use is recovered, for example, using a slender liquid supply means. Such a liquid supply means is made to contact the solution over a large area, and allows the solution to be left trapped in dents inside the cell, so that it is difficult to completely recover the solution. The present invention has an advantage that it allows the solution to be recovered almost completely.

Figure 11C:
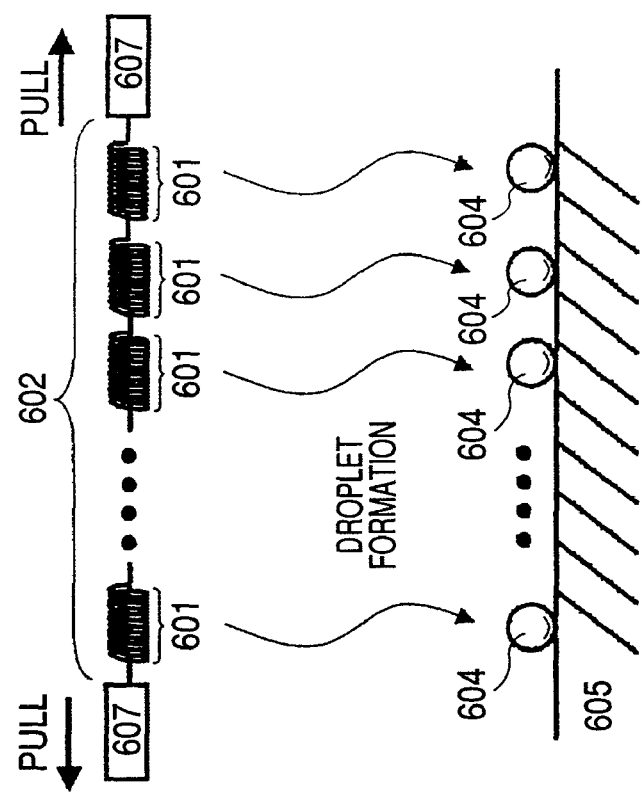
FIGS. 11A to 11C are schematic diagrams showing a method for forming many droplets according to an embodiment of the present invention.
Figure 11B:
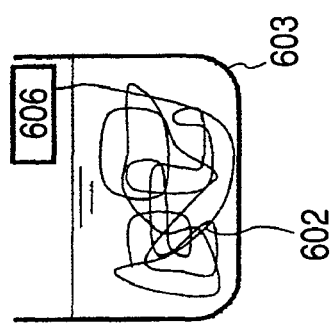
Figure 11A:
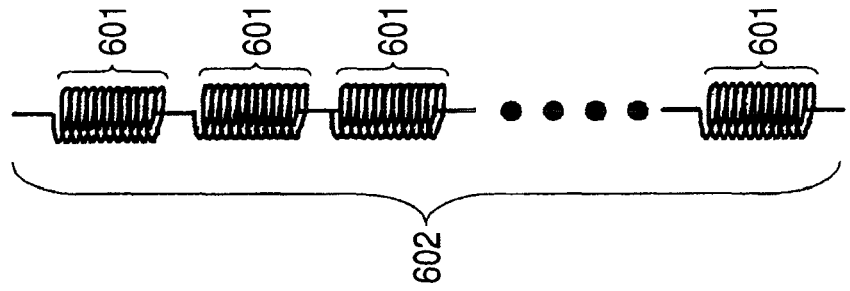

FIGS. 11A to 11C are schematic diagrams showing a method for forming plural droplets according to a fifth embodiment of the present invention. A droplet formation member 602 including, as shown in FIG. 11A, plural spiral droplet holders 601 and a transfer unit connecting the plural spiral droplet holders 601 is, as shown in FIG. 1B, immersed in the solution, out of which plural droplets are to be formed and which is contained in a container 603, using a handle 606. The number of the droplet holders 601 to be connected may range from, for example, 2 to 10,000 or so. The droplet formation member 602 as a whole can be bent and put in the small container 603. When the droplet formation member 602 immersed in the solution contained in the container 603 is pulled up, a droplet is formed at each of the plural droplet holders 601. When, using a deformation means 607 designed to deform the droplet holders by pulling at least one of the two ends of the droplet formation member 602, both ends of the droplet formation member 602 are, as shown in FIG. 11C, pulled away from each other, the plural droplets 604 are formed on a substrate 605 at a time. The droplet holders 601 each have a simple structure, so that they can be uniformly fabricated at low cost. Such inexpensive droplet holders can be used in a first step for forming uniform particles.

Figure 12:
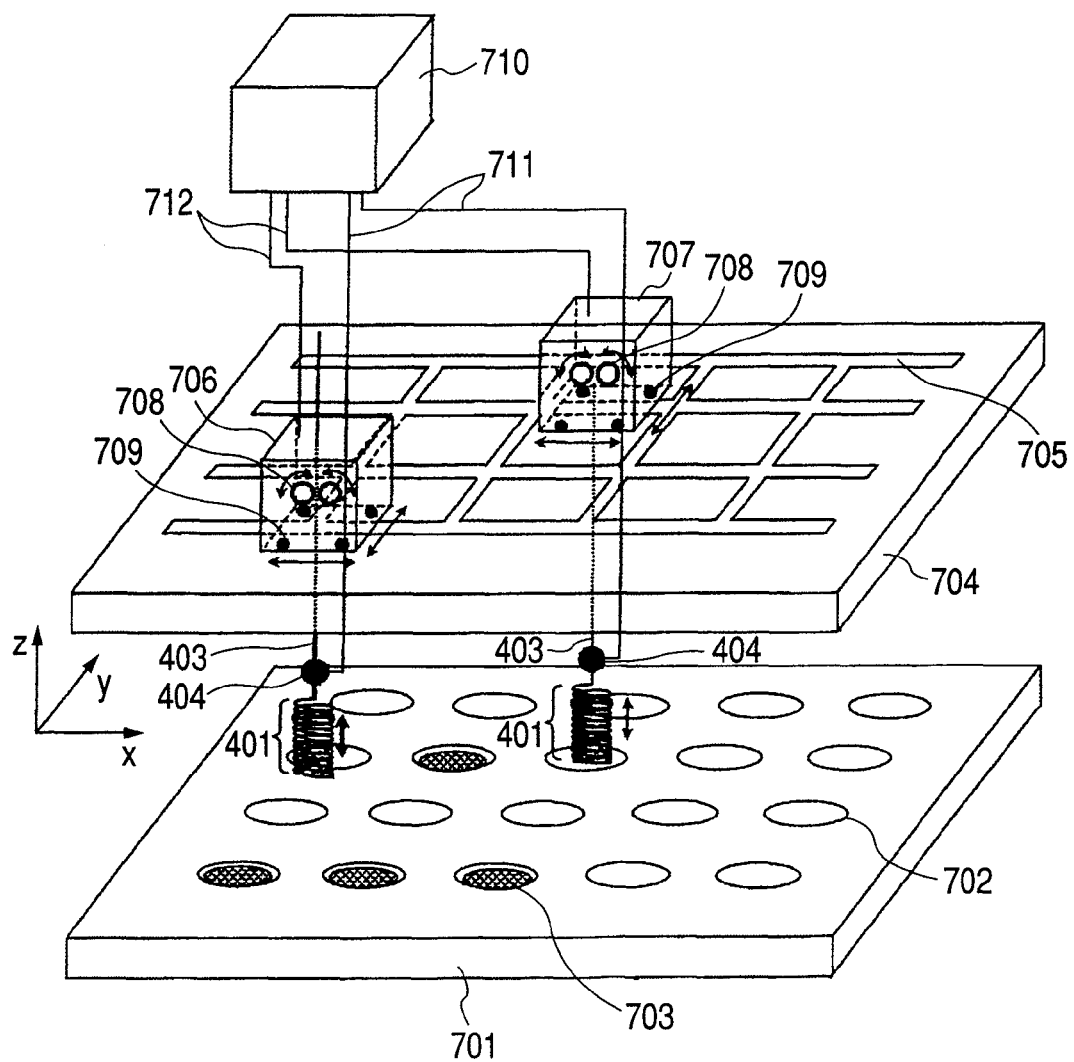
FIG. 12 is a schematic diagram showing a droplet transfer apparatus according to an embodiment of the present invention.

FIG. 12 shows an example system configuration according to a sixth embodiment of the present invention. The system is capable of executing a series of operations including droplet holding, transfer, dripping, and mixing concurrently. In this embodiment, as shown in FIG. 12, when there are plural wells 702 on a microplate 701, a solution 703 in a well 702 can be transferred to another well 702. The system enables concurrent solution transfers between the wells 702 by the use of a plurality of the spiral droplet holders 401. In the following, solution transfers between the wells 702 on the microplate 701 and external containers containing a solution will not be described, but it is obvious that such solution transfers can be performed using a configuration similar to that of the present embodiment.

In the present embodiment, the solution is transferred between containers using the spiral droplet holders 401 made of a shape-memory alloy as described for the third embodiment. The configuration of the present embodiment, therefore, includes a mechanism for moving the spiral droplet holders 401 over the microplate 701. Referring to FIG. 12, the spiral droplet holders 401 are connected to drive sections 706 and 707, respectively, via handles 403. The drive sections 706 and 707 can move over a drive section holding board 704 along guide slots 705. The guide slots 705 are formed through the thickness of the drive section holding board 704. Therefore, when the drive section 706 or 707 moves over the drive section holding board 704, the corresponding spiral droplet holder 401 also moves being positioned straight below the drive section 706 or 707. The drive sections 706 and 707 have spherical wheels 709 which enable the drive sections 706 and 707 to move over the drive section holding board 704 in either x or y direction. Even though, in the present embodiment, the spherical wheels 709 are used as moving means for the drive sections 706 and 707, a different method may be used, for example, a method in which magnets and electrodes are disposed on the drive section holding board 704 and the drive sections 706 and 707 are driven magnetically or electrically. The drive sections 706 and 707 also have internal wheels 708 used to move the droplet holders 401 in the z direction. Namely, when the wheels 708 of the drive sections 706 or 707 are rotated, the corresponding handle 403 moves up or down in the z direction. Heaters 404 are provided for use in changing the spiral pitches of the spiral droplet holders 401. This is to desirably transform the spiral droplet holders 401 into a linear shape so as to help the droplet held by each of the spiral droplet holders 401 drip into the target well 702. Since the heaters 404 are to control the temperatures of the spiral droplet holders 401, they may each include a Peltier device capable of temperature control.

How a droplet is transferred will be described next. First, the drive section 707 is moved to above the container containing the solution to be transferred. Next, with the heater 404 for the spiral droplet holder 401 associated with the drive section 707 switched off, that is, with the spiral pitch of the spiral droplet holder 401 not yet widened, the wheels 708 of the drive section 707 are driven until the spiral droplet holder 401 is lowered down to the bottom of the container. When the spiral droplet holder 401 is lowered to the bottom of the container allowing the surface of the spiral droplet holder 401 and the solution in the container to come into adequate contact, the solution comes into the inside of the spiral droplet holder 401. Subsequently, the wheels 708 are driven to lift the spiral droplet holder 401 from the microplate 701, and the drive section 707 is moved to straight above the target well 702 using the spherical wheels 709. After moving of the drive section 707 in the x and/or y direction is completed, the droplet holder 401 is lowered again, and the heater 404 is used to widen the spiral pitch of the spiral droplet holder 401 formed of a shape-memory alloy. This causes the droplet held by the spiral droplet holder 401 to drip into the target well 702. In FIG. 12, the drive section 706 is shown in a state of being moved in the x and/or y direction, and the drive section 707 is shown in a state immediately after a droplet is collected. It is possible to mix solutions by dripping a solution droplet into a container already containing a solution.

Next, how droplet operation is controlled will be described. In the present embodiment, the controller 710 controls plural drive sections (hence, plural droplet holders), allowing plural droplet operations including droplet transfer and mixing to be performed concurrently. In the present embodiment, with the number of the drive sections (droplet holders) unlimited in principle, complicated droplet operations can be concurrently performed with ease. Referring to FIG. 12, drive signal lines 712 are used to transmit signals for moving the droplet holders 401 in the x, y, and z directions from the controller 710 to the drive section 706 or 707. Temperature control lines 711 are used to supply electric current to the heaters. The signal lines may be coated metallic wires. Or, signals and power may be transmitted wirelessly. To keep the drive sections in a stable state, two drive section holding boards 704 may be used enabling the drive sections to be moved being sandwiched between the two boards. Furthermore, there may be plural microplates 701, and they may be removed as required. The droplet holders can be removed, cleaned, and replaced with ease.

Figure 13A:
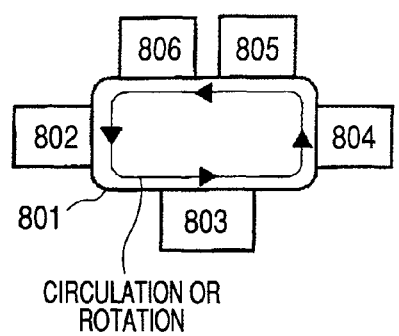
FIGS. 13A to 13H are schematic diagrams showing a blood biochemical analyzer according to an embodiment of the present invention.

FIGS. 13A to 13H are schematic diagrams showing principal parts of a blood biochemical analyzer according to a sixth embodiment of the present invention. FIG. 13A is a schematic diagram showing an example analyzer configuration. There is a sample circulator 801 at the center of the analyzer. The sample circulator 801 circulates through different parts while hanging many sample reaction jigs which function as sample holding means being described later. Devices associated with the different parts are disposed around the sample circulator 801. A sample to be analyzed, i.e. blood is contained in a test tube placed on a sample tray of a sample management device 802 which functions as a sample storage. As many sample reaction jigs as the number of inspection items are used to collect and hold respectively required volumes of blood for respective inspection items. The sample reaction jigs are circulated through the different parts by the sample circulator 801. At a reagent management device 803 which functions as a reagent supply means, reagents required for the respective inspection items are added to the samples held by the respective sample reaction jigs. Subsequently, the reactions of the samples to the reagents added to them are measured at a detection section 804. Waste samples held by the sample reaction jigs thus circulated are disposed of at a waste disposal device 805. The sample reaction jigs are then cleaned at a reaction jig cleaning device 806 and put in use again for blood sample measurement.

Figure 13B:
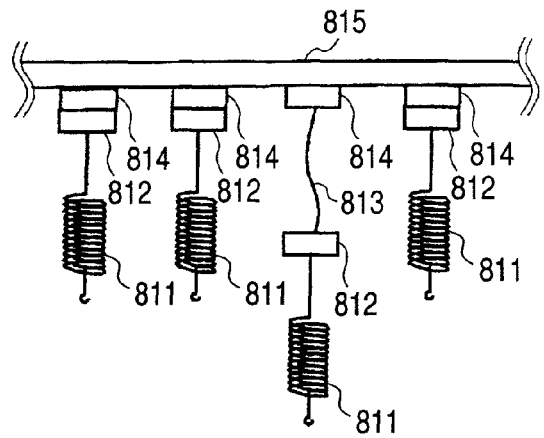

FIG. 13B is an enlarged view of a part of the sample circulator 801. The sample circulator 801 hanging the sample reaction jigs 811 circulates through the different parts. Each of the sample reaction jigs 811 is, as described above, a jig including an droplet holder and its peripheral parts. They can each hold fluid. The sample reaction jigs 811 shown in FIG. 13B each includes a spiral droplet holder and a projection for use in dripping the droplet. The sample reaction jigs are each hung from a circulation rail 815 via a reaction jig fixing section 812 and a rail fixing jig 814. They can travel along the circulation rail 815. Each pair of the reaction jig fixing section 812 and the rail fixing jig 814 are connected by an up-and-down line 813. Adjusting the length of the up-and-down line 813 pulled out between a pair of the reaction jig fixing section 812 and the rail fixing jig 814 moves the corresponding sample reaction jig 811 up and down.

Figure 13C:
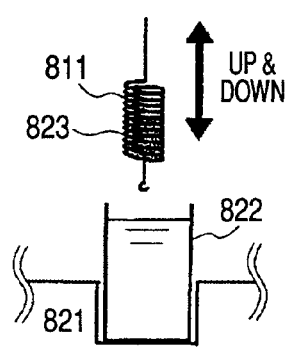

FIG. 13C is a schematic diagram showing an enlarged view of a part of the sample management device 802. Many test tubes 822 containing blood are held on a sample tray 821. The sample tray 821 operates by reacting to the sample reaction jigs 811. Namely, it positions each of the test tubes containing the sample required by the corresponding sample reaction jig 811 immediately below the corresponding sample reaction jig 811. The sample circulator 801 moves the sample reaction jigs 811 up and down thereby allowing each of the sample reaction jigs 811 to collect and hold a prescribed volume of a predetermined blood sample. The sample reaction jig 811 shown in FIG. 13C holds blood in a portion of its droplet holder. This is done by controlling the depth to which the sample reaction jig 811 is immersed in the blood. Even though only one test tube and one sample reaction jig are shown in FIG. 13C, in real operation, as many sample reaction jigs as the number of required inspection items are made to collect prescribed blood samples from many test tubes and hold them. The sample circulator 801 sequentially sends blood 823 held by the sample reaction jigs 811 to the reagent management device 803.

Figures 13D, 13E:
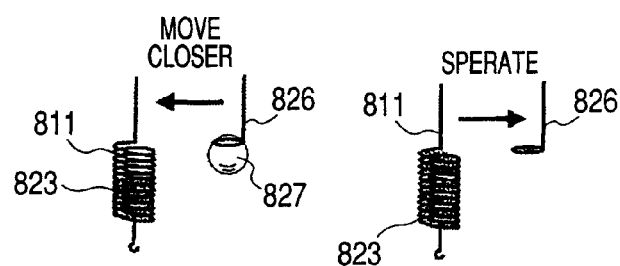

FIGS. 13D and 13E are schematic diagrams showing how a reagent 827 is added to the blood 823 at the reagent management section 803. To have the reagent 827 held by a reagent holding jig 826, a device incorporating the arrangement shown in FIGS. 5A to 5C may be used. The reagent holding jig 826 holding the reagent 827 is moved toward the sample reaction jig 811 that holds the blood 823 transferred to the reagent management section 803 by the sample circulator 801 until the reagent 827 and the blood 823 come into contact. When the reagent holding jig 826 is subsequently moved away from the sample reaction jig 811, the reagent 827 is transferred to the sample reaction jig 811 to be mixed with the blood 823. This creates a mixed solution 828 of the reagent 827 and the blood 823. In the mixed solution 828, a chemical reaction corresponding to the inspection item takes place. The result of the chemical reaction is inspected at the inspection section 804. In the present example described above, one reagent 827 and one sample reaction jig 811 are used. In real operation, plural reagents corresponding to plural inspection items may be mixed to cause plural reactions.

Figure 13F:
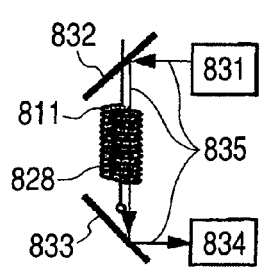
Figure 13G:
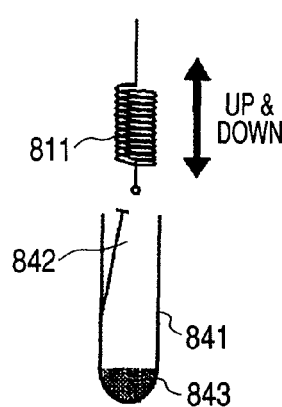
Figure 13H:
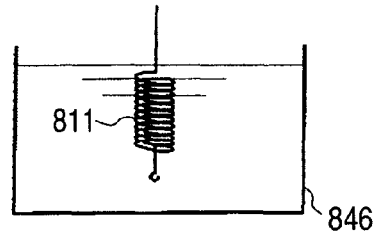

FIG. 13F is a schematic diagram of the inspection section 804. Even though the present invention is being described with absorbance measurement in mind, the present invention can also be applied to other kinds of measurement, for example, optical measurements making use of fluorescence emission or optical scattering. Light emitted from a light source 831 advances along a light path 835. After being reflected by mirrors 832 and 833 installed along the light path 835, the light is received by a photomultiplier tube 834. On its way to the photomultiplier tube 834, the light passes through the mixed solution 828 of blood and reagent held by the sample reaction jig 811 thereby undergoing optical absorption at a wavelength corresponding to the target inspection item. The optical absorption can be analyzed based on the output of the photomultiplier tube 834. The solution having been inspected is sent to the waste disposal device 805. FIG. 13G is a schematic diagram of the waste disposal device 805. Hooking an end of the sample reaction jig 811 to a projection 842 projecting from the waster container 841 and moving the sample reaction jig 811 up and down causes waste liquid 843 to drip into the waste container 841. Subsequently, the sample circulator 801 sends the sample reaction jig 811 to the reaction jig cleaning device 806. FIG. 13H is a schematic diagram of cleaning in the reaction jig cleaning device 806. The sample reaction jig 811 is cleaned in a cleaning tank 846. In cleaning the sample reaction jig 811, ultrasonic waves may be used to clean it more effectively. The sample reaction jig 811 thus cleaned is put in use again. In cases where contamination is a critical concern, a device in which the used sample reaction jig is, instead of being cleaned, replaced with a new one may be used.

As shown in FIGS. 13A to 13H, the liquid transfer unit is applicable to an automatic blood analyzer. Automatic blood analysis can be performed using an inexpensive simple configuration incorporating many inexpensive and simple-structured sample reaction jigs 811. Even in cases where different inspection items involve different reaction times and temperatures, the liquid transfer unit can easily be made compatible by incorporating a loop arrangement and a temperature-controlled bath in the sample circulator.

The present invention has been described by way of embodiments in which annular or spiral droplet holders are used, but the applicability of the present invention is not limited to the two types of droplet holders. The present invention can also be applied to droplet holders having a similar structure capable of holding a droplet. Such droplet holders include those in which two or more parts are combined to form a space for holding a droplet. Considering that a smaller droplet evaporates faster, it will be effective to accommodate the entire droplet transfer unit in a closed chamber or a humidified chamber, or to install such a chamber in the vicinity of the droplet holder so as to prevent droplet evaporation as required.

What is claimed is:

1. A droplet transfer unit, comprising:
a droplet holder formed of wire having a spiral shape and made of a shape-memory alloy, thereby configured to inscribe a droplet within the droplet holder;
a heater connected to the droplet holder;
a controller configured to control the heat of the heater; and
a moving unit configured to move the droplet holder.

2. The droplet transfer unit according to claim 1, wherein the droplet holder is configured to inscribe the droplet such that a volume V of the droplet inscribed by the droplet holder satisfies the following equation:

$$V = \pi d^2/4 \times p \times n$$

where n, d, and p represent a number of turns, a diameter, and a pitch of the spiral.

3. The droplet transfer unit according to claim 1, wherein the droplet holder has a projection at an end thereof.

4. The droplet transfer unit according to claim 3, further comprising:
a well for storing the droplet, and
a projection provided on the well, the projection on the well being configured to be hooked to the projection at an end of the droplet holder.

5. The droplet transfer unit according to claim 1, wherein the droplet transfer unit has a plurality of droplet holders.

6. The droplet transfer unit according to claim 1, wherein the moving unit includes a plurality of supports, each support being connected to an end of the droplet holder formed of wire having a spiral shape, wherein at least one support is configured to enable adjustment of a length of the droplet holder.

7. A light detection device, comprising:
a droplet holder formed of wire having a spiral shape, thereby configured to hold a droplet;
a light irradiation configured to irradiate light through an inside of the spiral shape of the droplet holder; and
a detection unit configured to detect light irradiated through the inside of the spiral shape of the droplet holder;
wherein the droplet holder is disposed between the light irradiation unit and the detection unit.

8. The light detection device according to claim 7, further comprising:
a plurality of substantially transparent members configured to sandwich the droplet holder.

9. The light detection device according to claim 7, further comprising:
a container configured to recover the droplet; and
a projection provided on the container;
wherein the projection provided on the container configured to deform the droplet holder by being hooked to a substantially middle portion of the droplet holder, or a vicinity thereof.

10. A container, comprising:
a droplet transfer unit that includes
a droplet holder formed of wire and configured to inscribe a droplet within the droplet holder, and
a moving unit configured to move the droplet holder,
wherein the droplet holder is spiral-shaped, and
wherein the droplet holder has a projection at an end thereof;
a well configured to store the droplet; and
a projection provided on the well, the projection provided on the well being configured to be hooked to the projection at an end of the droplet holder.

11. The light detection device according to claim 10,
wherein the moving unit includes a plurality of supports, each support being connected to an end of the droplet holder formed of wire having a spiral shape, wherein at least one support is configured to enable adjustment of a length of the droplet holder.

12. The container according to claim 10,
wherein the droplet transfer unit further includes a plurality of supports, each support being connected to an end of the droplet holder formed of wire having a spiral shape, wherein at least one support is configured to enable adjustment of a length of the droplet holder.

* * * * *